US00PP30635P2

(12) United States Plant Patent
Hansen

(10) Patent No.: US PP30,635 P2
(45) Date of Patent: Jul. 2, 2019

(54) ***BUDDLEIA* PLANT NAMED 'LAVENDER CASCADE'**

(50) Latin Name: *Buddleia davidii*
Varietal Denomination: Lavender Cascade

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/932,774

(22) Filed: Apr. 23, 2018

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./242

CPC ... A01H 5/02; A01H 5/00; A01H 5/08; A01H 5/0812; A01H 6/30
See application file for complete search history.

(56) References Cited

PUBLICATIONS

Plants Delights Nursery New Cascades Butterfly Bushes not your grandmothers buddleias 2017, retrieved on Mar. 25, 2019, retrieved from the Internet at http://blog.plantdelights.com/new-cascade-butterfly-bushes-not-your-grandmothers-buddleias/, 4 pp. (Year: 2017).*

* cited by examiner

*Primary Examiner* — June Hwu

(57) ABSTRACT

The new and distinct plant of *Buddleia* 'Lavender Cascade' is a rounded-mounded, multi-stemmed, winter-hardy butterfly bush with very long, narrow, slightly drooping, flowering thyrse producing a waterfall effect over a long season beginning mid-summer with sweetly-fragrant flowers of light purple petals that are attractively offset by dark green foliage with silvery undersides. The new plant is valuable for landscaping en masse, as an accent or as a potted specimen.

1 Drawing Sheet

Botanical classification: *Buddleia davidii.*
Variety denomination: 'Lavender Cascade'.

BACKGROUND OF THE PLANT

The present invention relates to the new and distinct butterfly bush plant of the Scrophulariaceae family, *Buddleia* 'Lavender Cascade'. 'Lavender Cascade' is the result of an ongoing breeding program conducted by the inventor. The goals for this program have been to produce improved, garden-worthy plants for the ornamental plant market. The new plant, was assigned the breeder code 14-38-7, is a single seedling selection from a cross between the unreleased proprietary hybrid 11-34-01 (not patented) as the female or seed parent collected by Hans A. Hansen in the fall of 2014 at a wholesale perennial nursery in Zeeland, Mich., USA. The male parent was 'Wisteria Lane' U.S. Plant Pat. No. 27,833. The new cultivar was selected as single individual flowering plant within the progeny of the above stated controlled-pollination during the summer 2015 in a controlled environment at the same nursery in Zeeland, Mich.

No plants of *Buddleia* 'Lavender Cascade' have been sold, under this or any other name, in this country or anywhere in the world, prior to the filing of this application, nor has any disclosure of the new plant been made prior to the filing of this application with the exception of that which may have been sold or disclosed within one year of the filing date of this application and was either derived directly or indirectly from the inventor.

*Buddleia* 'Lavender Cascade' was first asexually propagated from a single select plant in 2015 by stem cuttings at the same nursery in Zeeland, Mich. The resultant asexually propagated plants have been found to be stable and true to type in successive generations of asexual reproduction.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

In comparison to the new plant the female parent has a deeper cerise-pink to raspberry-pink flower color and is upright in habit. The male plant has a more pendulous thyrse with wider spacing of the flowers.

The nearest comparison plants known to the inventor are *Buddleia* 'Lavender Cupcake' U.S. Plant Pat. No. 28,221, 'Wisteria Lane' U.S. Plant Pat. No. 27,833, 'Butterfly Heaven' U.S. Plant Pat. No. 19,935 and the two co-pending applications from the same inventor 'Grand Cascade' (U.S. Plant patent application Ser. No. 15/932,773) and 'Pink Cascade' (U.S. Plant patent application Ser. No. 15/932,743). 'Lavender Cupcake' is a smaller plant in habit and thyrse size and has different colored flower petals. 'Wisteria Lane' is shorter in habit with smaller thyrse and the branches are more drooping instead of mainly the thyrse drooping and the petals are light purple. 'Butterfly Heaven' is shorter and narrower in habit, with less drooping of the thyrse, and the thyrse is shorter and narrower and the petals are light violet. 'Grand Cascade' is larger in habit and has longer and broader thyrse with petals that are different colored. 'Pink Cascade' has flower petals that are light purple with more pinkish hue. Other similar plants include 'Tobudviole' U.S. Plant Pat. No. 22,063 which has a more compact habit, shorter thyrse and smaller foliage; and 'TOBUD0615' U.S. Plant Pat. No. 23,461 which is more compact with smaller leaves and shorter thyrse that lack the drooping of the new plant.

*Buddleia* 'Lavender Cascade' is a unique winter-hardy butterfly bush different from all other *Buddleia* cultivars known to the inventor based on the following combined repeatedly observed distinguishing traits:

1. Winter-hardy butterfly bush shrub, with multiple-stemmed, well-branched, rounded, waterfall-type arching, mounded habit.
2. Large, narrow, many-flowered, elongated and slightly-drooping thyrse flowering over a prolonged season beginning mid-summer.
3. Flowers with light purple petals.
4. Lanceolate foliage of dark green with silvery undersides.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
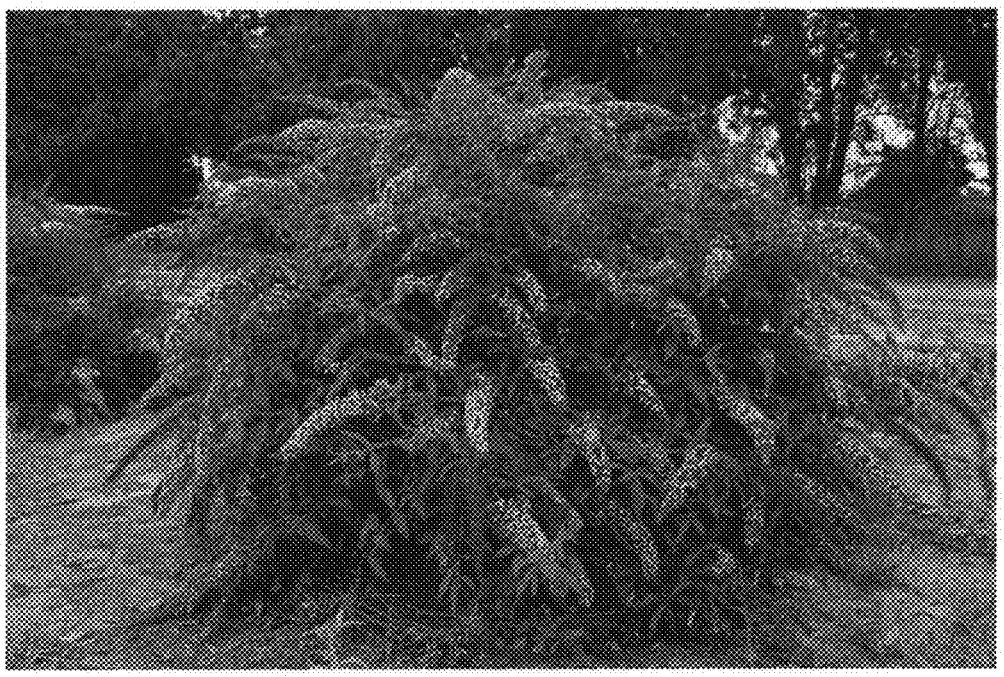
FIG. 1 shows the habit of a three-year-old plant in mid-season flowering.
Figure 2:
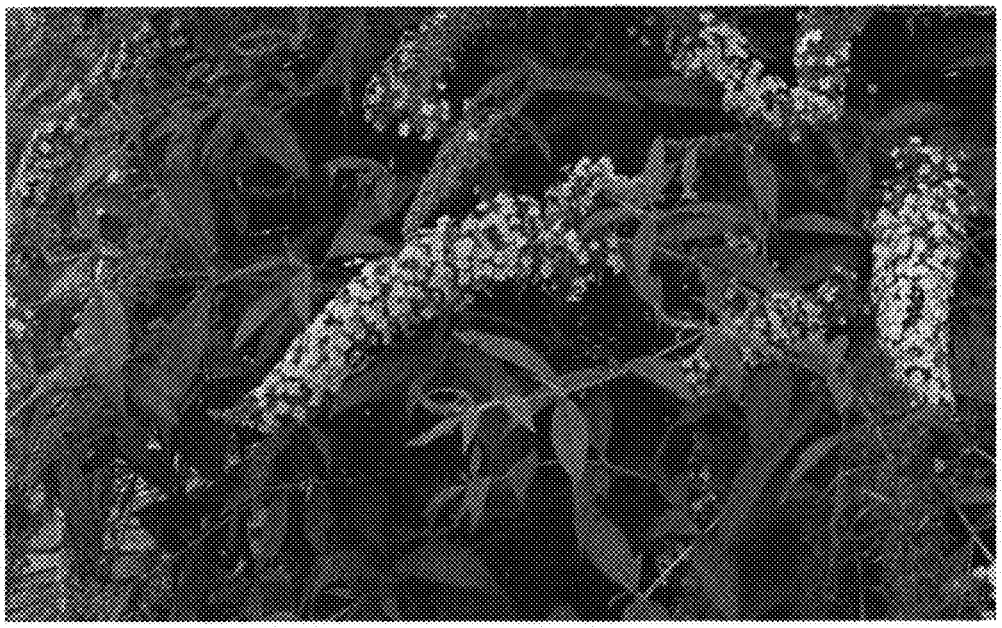
FIG. 2 shows a close-up of the inflorescence.

The following descriptions and color references are based on the 2015 edition of The Royal Horticultural Society Colour Chart except where common dictionary terms are used. The new plant, *Buddleia* 'Lavender Cascade', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand, open-sun, field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in early spring.

Parentage: Unreleased proprietary hybrid 11-34-01 (not patented) as the female or seed patent; the male or pollen parent is a seedling of 'Wisteria Lane';

Propagation:

*Method.*—Softwood shoot cuttings.

*Time to initiate roots from tissue culture.*—About two weeks.

*Rooting habit.*—Normal, dense and branching, developing thick at base to about 1.5 cm diameter.

*Root color.*—Creamy white between RHS 159A and lighter than RHS 159 D depending on soil type.

*Crop time.*—Under normal summer growing conditions 12 to 15 weeks to flower in a four-liter container from cutting. Plant vigor is very good.

Plant description:

*Plant shape and habit.*—Winter-hardy, herbaceous to semi-woody, well-branched shrub with about 20 thick upright and branched main stems producing a rounded mound, to about 175 cm tall and about 260 cm wide.

*Stem.*—Terete and woody in lower portion, with exfoliating bark; younger upper portion tomentose to tomentulose; strong and flexible, arching or drooping; average about 155 cm tall from soil line to just below terminal flowers, and about 15.0 mm diameter at the base; about 24 branches per main stem before distal flowers in upper 12 nodes, extending at about 45° angle from main stem.

*Stem color.*—Young distal portion just below flowers nearest RHS 148D; basal 15 cm between RHS 200C and RHS 165B with striations between RHS 200A and RHS N199B.

*Internode.*—About 18 nodes per main stem below terminal thyrse, average internode length about 8.0 cm on unpinched plant; upper internodes slightly more elongated than lower internodes.

Foliage description: Opposite; lanceolate; decussate; serrate with about four to five teeth per cm, teeth about 1.5 mm long and 2.5 mm wide; young expanding leaves puberulent abaxial and adaxial, becoming glabrous adaxial; attenuate to cuneate base and acute apex; sessile; no foliar fragrance detected;

*Leaf blade size.*—Up to about 13.0 cm long and about 37.0 mm wide, average about 8.0 cm long and about 25.0 mm wide; becoming smaller in distal portion of stem.

*Foliage color.*—Young expanding leaf adaxial distal one-half nearest RHS 137A, basal one-half between RHS 191B and RHS 191C, young expanding abaxial nearest RHS 192A with argenteous base; mature leaves adaxial between RHS 137A and RHS 139A, mature abaxial between RHS 191B and RHS 191C.

*Veins.*—Reticulate; abaxial costate, puberulent; adaxial glabrous, slightly impressed.

*Vein color.*—Abaxial midrib and secondary veins blend between RHS 194B and RHS 148D; adaxial midrib and secondary veins nearest RHS 146D; expanding abaxial veins nearest RHS 196D and adaxial between RHS 191B and RHS 191C.

*Petioles.*—Leaves sessile.

*Inflorescence description.*—Glomerate thyrse consisting of about 1,000 to 2,000 self-cleaning salverform flowers; to about 26.0 cm long and about 7.0 cm across, average about 22.0 cm long and 6.5 cm across; beginning in mid-July and continuing until frost in Michigan.

*Inflorescence attitude.*—Slightly drooping.

*Flower buds.*—Elongated clavate with long tubular base, apex rounded; one day prior to opening about 14.0 mm long, about 2.5 mm diameter in club, tube about 1.0 mm diameter and about 8.0 mm long.

*Flower bud color.*—Between RHS 83D and RHS 83C in club portion, tube nearest RHS N77C.

*Sepals.*—Typically four, proximal two-thirds connate, adpressed to corolla tube; acute apex; glabrous adaxial and pubescent abaxial; margin entire; fused in about the basal 2.0 mm and split in about the terminal 1.5 mm, individually less than about 1.0 mm wide at point of fusion; forming a corolla about 3.5 mm long and about 2.0 mm across.

*Sepal color*.—Adaxial and abaxial nearest RHS 138A along center longitudinal axis with blush of nearest RHS N186C both abaxial and adaxial.

*Flowers*.—Salverform; actinomorphic; to about 17.0 mm long and 7.5 mm wide at face; with straight terete tube about 9.0 mm long and 1.0 mm diameter, and a abruptly applanate face about 7.0 mm across; attitude outward from thyrse center.

*Flowers fragrance*.—Pleasantly and distinctly sweet.

*Petals*.—Typically four; glabrous abaxial and on adaxial blades and tube, puberulent center abaxial tube; blade rounded with crenate margin; apex rounded; blade to about 3.0 mm across and about 3.0 mm long from fused face.

*Petal color*.—Upon opening and when fully open adaxial tube base between RHS 145D and RHS 157D, distal one half tube center between RHS 166C and RHS 164A, adaxial face blade nearest RHS N82C; upon opening and when fully open abaxial tube base nearest RHS 145D, distally tube nearest RHS N77B and abaxial petal blades nearest RHS N82C.

*Gynoecium*.—Pistil: one; about 5.0 mm long. Style: short, round, glabrous; about 1.5 mm long and less than 0.2 mm diameter; color nearest RHS 145D. Stigma: narrow ellipsoidal, minutely puberulent; about 0.2 mm in diameter and about 1.5 mm long; color nearest RHS 145A. Ovary: superior; oblong globose; about 1.0 mm across at base and 2.0 mm tall; distally tapering to style; color nearest RHS 143C.

*Androecium*.—Typically four. Filaments: none or less than 0.2 mm long and less than 0.1 mm diameter; when present color nearest RHS NN155D. Anthers: typically four; oblong; introrse; adnate to about mid-point of corolla tube; about 1.0 mm long and 0.5 mm wide; color nearest RHS 158A. Pollen: globose, less than 0.1 mm long; color nearest RHS 155B.

*Pedicel*.—Short, puberulent; about 2.0 mm long and about 0.3 mm diameter; color nearest RHS 138A.

*Peduncle*.—Quadrangular; tomentulose to tomentose, flexible and strong; to about 37.0 cm long, and about 3.0 mm across at base below flowers.

*Peduncle color*.—Between RHS N187A and RHS N187B.

*Fruit*.—Moderate to heavy fruit set; oblong with acute apex; attenuate base; glabrous, bi-valved, septicidal capsule; about 11.0 mm long and about 1.8 mm diameter toward apex and 1.0 mm toward base.

*Fruit color*.—As maturing nearest RHS 187A; when mature and dehiscing nearest RHS 164B.

*Seed*.—Elongated linear with sharply acute ends; about 1.5 mm long and less than 0.2 mm across in center.

*Seed color*.—Nearest RHS 200A.

Disease resistance: Resistance has been noted to deer browsing. Other pest and disease resistance beyond that common to butterfly bush cultivars has not been observed. The plant grows best with plenty of moisture and adequate drainage, but is able to tolerate some drought when mature.

Hardiness at least from USDA zone 6 through 10.

It is claimed:

1. A new cultivar of winter-hardy butterfly bush plant named *Buddleia* 'Lavender Cascade' as herein illustrated and described.

* * * * *